(12) United States Patent
Thomson et al.

(10) Patent No.: US 9,849,266 B2
(45) Date of Patent: Dec. 26, 2017

(54) AGENT DELIVERY CATHETER

(71) Applicant: Brainlab AG, Munich (DE)

(72) Inventors: Rowena Thomson, Kirchheim (DE); Martin Rube, Zorneding (DE); Stephan Mittermeyer, Landshut (DE)

(73) Assignee: Brainlab AG, Munich (DE)

( * ) Notice: Subject to any disclaimer, the term of this patent is extended or adjusted under 35 U.S.C. 154(b) by 0 days.

(21) Appl. No.: 15/120,307

(22) PCT Filed: Feb. 20, 2014

(86) PCT No.: PCT/EP2014/053320
§ 371 (c)(1),
(2) Date: Aug. 19, 2016

(87) PCT Pub. No.: WO2015/124188
PCT Pub. Date: Aug. 27, 2015

(65) Prior Publication Data
US 2017/0056617 A1   Mar. 2, 2017

(51) Int. Cl.
*A61M 5/32*    (2006.01)
*A61M 25/00*   (2006.01)
*A61M 25/01*   (2006.01)
*A61M 25/04*   (2006.01)

(52) U.S. Cl.
CPC ........ *A61M 25/008* (2013.01); *A61M 25/002* (2013.01); *A61M 25/0102* (2013.01);
(Continued)

(58) Field of Classification Search
CPC ............ A61M 25/0102; A61M 25/002; A61M 25/0108; A61M 25/0127; A61M 25/04;
(Continued)

(56) References Cited

U.S. PATENT DOCUMENTS

| 6,562,021 | B1* | 5/2003 | Derbin ................... A61B 18/14 604/523 |
| 6,632,184 | B1* | 10/2003 | Truwit ............. A61M 25/0102 600/434 |
| 7,815,623 | B2* | 10/2010 | Bankiewicz ....... A61B 17/3417 604/506 |
| 8,337,458 | B2 | 12/2012 | Bankiewicz et al. |

(Continued)

FOREIGN PATENT DOCUMENTS

| EP | 2558154 A2 | 2/2013 |
| WO | 2007024841 A2 | 3/2007 |
| WO | 2008144585 A1 | 11/2008 |
| WO | 2011130107 A2 | 10/2011 |

OTHER PUBLICATIONS

International Search Report, dated Nov. 17, 2014, 2 pages.

*Primary Examiner* — Kevin C Sirmons
*Assistant Examiner* — Leah Swanson
(74) *Attorney, Agent, or Firm* — Tucker Ellis LLP (57) ABSTRACT

An agent delivery catheter including a first hollow tube and a second hollow tube that protrudes from a distal opening of the first hollow tube and defines an agent delivery lumen extending along the entire length of the catheter. The distal end of the first tube is coupled to the second tube to form an annular cavity between the first tube and the second tube, the annular cavity provided for accommodating a retractable stylet shaft. An adapting member is disposed on and coupled to a proximal end of a ceramic member and for receiving a distal end of the stylet shaft.

20 Claims, 4 Drawing Sheets

(52) U.S. Cl.
CPC .... *A61M 25/0108* (2013.01); *A61M 25/0127* (2013.01); *A61M 25/04* (2013.01); *A61M 2025/0042* (2013.01); *A61M 2205/0211* (2013.01); *A61M 2210/0693* (2013.01)

(58) Field of Classification Search
CPC ............ A61M 25/0194; A61M 25/008; A61M 25/0068; A61M 25/0026; A61M 2025/0004; A61M 2025/0006; A61M 2025/0039; A61M 2025/004; A61M 2025/0063; A61M 2205/0211; A61M 2210/0693
USPC ................. 604/175, 510, 523–525, 528, 529
See application file for complete search history.

(56) References Cited

U.S. PATENT DOCUMENTS

| | | | | |
|---|---|---|---|---|
| 2005/0080398 | A1* | 4/2005 | Markel | A61M 25/0014 604/508 |
| 2005/0277889 | A1* | 12/2005 | Neidert | A61M 25/0097 604/181 |
| 2006/0235355 | A1* | 10/2006 | Freas | A61B 90/11 604/164.05 |
| 2008/0183128 | A1* | 7/2008 | Morriss | A61M 3/0283 604/35 |
| 2013/0030408 | A1* | 1/2013 | Piferi | A61B 5/055 604/500 |

\* cited by examiner

AGENT DELIVERY CATHETER

RELATED APPLICATION DATA

This application is a national phase application of International Application No. PCT/EP2015/053320 filed Feb. 20, 2014 and published in the English Language.

The present invention relates to catheters which can be used to infuse therapeutic agents into solid tissue, i.e. using convection enhanced delivery (CED), which is understood to mean pressing-driven infusions, in particular into the central nervous system, specifically into the brain of a patient, and which can remain in place over a longer period of time.

In order to place such catheters within the tissue to be treated, the catheter is inserted through an access opening, for example an opening in the skull of a patient, and advanced from this access point in a straight trajectory directly through the tissue until the distal opening of the catheter, from which the therapeutic agent is to be dispensed, reaches the target region.

WO 2011/130107 shows a cannula for delivering a therapeutic agent, comprising a rigid ceramic support sleeve which extends over a substantial length of the cannula and assists in advancing the cannula, by means of a trajectory device placed on a patient's head, to a position from which the therapeutic agent is to be dispensed.

In order to allow infusion over a longer period of time, delivery catheters can comprise a tubing made of flexible polymer materials which allow so-called "tunnelling", in which the part of the catheter outside the patient's skull is bent substantially at a right angle and positioned so as to extend beneath the scalp to a position away from the access site, wherein the skin over the access site is then closed.

A major disadvantage of such flexible tubing material is that it is too flaccid to be pushed in a straight trajectory through the tissue to the target region, such that stylets have to be used to increase the rigidity of the flexible portions of the catheter during the placement procedure. The stylet is then withdrawn from the catheter once the catheter tip has been placed in the target region, leaving behind the flaccid portion of the catheter which is then able to conform to the patient's anatomy.

The catheter is often inserted into homogenous tissue, and even using a catheter stylet often cannot ensure that the catheter does not deviate from the planned trajectory and accurately reaches the target region, hence it is desirable to know the actual position of the catheter, in particular the catheter tip, during this procedure.

It is the object of the present invention to provide a catheter, the position of which can be reliably and yet safely determined during placement.

This object is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

The agent delivery catheter of the present invention as described herein can be used within the context of the products iPlan® and/or VarioGuide™ as distributed by Brainlab AG, as well as within the context of the product ClearPoint®, in order to deliver therapeutic agents directly to brain tissue. Specifically, the catheter can be used with universal instrument holders such as Brainlab's VarioGuide™, tracking cameras such as Brainlab's Curve™, Kick® and Kolibri®, or other means for the tracking of devices, such as Brainlab's Kick® EM. It can also be used together with user interfaces and pre-operative and/or intra-operative planning software such as iPlan® and the Cranial Software platform. In addition, it can be seen in intra-operative images using modalities including but not limited to X-ray, ultrasound, computed tomography (CT) and magnetic resonance (MR) imaging.

Since the effective delivery of therapeutic agents via the vasculature of the brain is significantly affected by the presence of the blood-brain barrier, directed drug delivery such as convection-enhanced delivery (CED) is applied in order to enhance the transport of compounds across the blood-brain barrier. Specifically, convection-enhanced delivery uses positive pressure to distribute therapeutic agents from an infusion cannula through brain parenchyma, such that a high local concentration of the delivered therapeutic agent at a target volume is obtained, while still maintaining a homogeneous concentration profile. It is however necessary to precisely position the catheter and effectively distribute the therapeutic agent, and to cover the target region to be treated by the therapeutic agent. In addition, leakage into subarachnoid or intraventricular spaces is to be avoided. As will be shown further below, the catheter of the present invention can be used within the context of catheter trajectory guiding devices and within the context of frameless image-guided placement procedures.

In particular, and as will be shown further below, the present invention provides a catheter which is in particular configured to deliver a therapeutic agent to a target side and which is easy to handle, minimises trauma and therefore helps to prevent a dispensed fluid from flowing back along the outer surface of the catheter, but without the use of multiple large "stepped" backflow barriers on the outer surface of the catheter, wherein "large" is understood here to mean a step exhibiting a ratio of more than 1:2 between a (smaller) outer diameter before the step and a (larger) outer diameter after the step.

The agent delivery catheter of the present invention comprises a first hollow tube and a second hollow tube which protrudes from a distal opening of the first hollow tube and defines an agent delivery lumen extending along the entire length of the catheter, wherein: the distal end of the first tube is coupled to the second tube to form an annular cavity between the first tube and the second tube; the annular cavity is configured to accommodate a retractable stylet shaft; a ceramic member which is disposed at the distal end of the first tube, in particular distally with respect to the distal opening of the first tube, encompasses the second tube and couples the first tube to the second tube, in particular via a third hollow tube which encompasses the first tube and the ceramic member; and a protective shrink-fit tube is disposed radially on the outside of the ceramic member and extends over at least the length of the ceramic member.

In other words, the agent delivery catheter of the present invention comprises a capillary (second) tube through which the therapeutic agent is delivered to a desired region once the distal opening of said capillary tube has been advanced to a desired region. This tube can also be pre-primed with the therapeutic agent or any other suitable fluid in order to avoid infusing air into the patient's tissue or air bubbles into the infusate, both of which can cause an unpredictable distribution of the infusate.

In order to protect the (second) tube, which can in particular be a PEEK tube, from kinking when the "tunnelled" catheter is positioned so as to extend out of an opening in the patient's skull and then underneath the patient's scalp, a further (first) tube, which is in particular a co-extruded PEBAX tube, is provided around the capillary tube and can extend over a substantial length of the capillary tube. The first tube is coupled to the second tube, for example by bonding, such that a rotationally symmetrical annular cavity is formed between the first tube and the second tube, into which a retractable stylet shaft can be introduced for advancing the catheter through the patient's tissue.

The coupling between the first tube and the second tube comprises a ceramic member which comprises a ceramic material, in particular alumina, and specifically contains high-purity alumina (greater than 99%, for example 99.8%), and which can be clearly detected in ultrasound, MR and CT images and can therefore aid in determining the position of the distal portion of the catheter during a placement procedure. Conversely, the cavity formed between the first tube and the second tube can also be detectable in ultrasound, MR and CT images, since the cavity may be filled with air after the stylet shaft has been withdrawn from the cavity. The ceramic member can be disposed around the first tube, distally with respect to the distal opening of the first tube. Due to the brittle properties of ceramic materials, a protective layer is provided in the form of a (thermal) shrink-fit tube which can be made of PET and which is disposed around the ceramic member over at least its entire length. This enables the ceramic member to be withdrawn from the tissue in one piece together with the catheter even after breakage or damage to the ceramic components has occurred. Any ceramic components of the catheter of the present invention can be protected by such shrink-fit tubes which maintain the integrity of the ceramic components and therefore also the catheter after damage to the brittle ceramic components has occurred, in order to avoid injury to the patient.

It is also possible for the ceramic member to not be directly attached to the first tube but rather coupled to the first tube via a third tube which extends radially on the outside of the second tube and which can be bonded to the first tube and the ceramic member.

In accordance with a preferred embodiment of the present invention, the second tube protrudes from a distal opening of the ceramic member, wherein a stiffening tube which is in particular disposed radially between the second tube and the ceramic member protrudes from the distal opening of the ceramic member and extends over at least a part of the protruding portion of the second tube. In order to make the catheter of the present invention easier to handle, the first tube, the second tube and/or the stylet shaft which is introduced into the cavity formed between them can comprise depth markers which indicate the depth to which the catheter has already been introduced into an anatomical structure.

The stiffening tube prevents the capillary tube from bending or indeed kinking while the catheter is being placed and therefore assists in precisely targeting the catheter. The distal end of the stiffening tube can also form a significant step or increase in the catheter diameter, depending on the wall thickness of the stiffening tube, which then prevents the therapeutic agent from undesirably flowing back along the outer surface of the catheter tip.

It is also conceivable for the catheter to comprise an adapting member which is disposed on and coupled to a proximal end of the ceramic member and configured to receive a distal end of the retractable stylet shaft, wherein the adapting member is in particular configured to be releasably secured to the distal end of the stylet shaft by means of a positive fit or a frictional fit.

Such an adapting member can generally aid in connecting a stylet shaft to the distal portion of the catheter, in particular if the adapting member is made of a plastic material which is more pliable than a ceramic material and therefore allows a frictional fit or positive fit to be provided between the adapting member and the distal end of a stylet shaft.

For this purpose, the adapting member can comprise a circumferential inner surface which is configured to establish a frictional fit or positive fit between the distal end of the stylet shaft and the adapting member. Providing such a positive fit or frictional fit enables the catheter to be withdrawn together with the stylet to a certain degree, for example when the position of the catheter tip has to be corrected.

In accordance with another preferred embodiment of the present invention, the adapting member comprises a protrusion which extends centrally in a distal direction from a distal end of the adapting member into a proximal opening of the ceramic member. Providing such a protrusion not only aids in precisely attaching the adapting member to the ceramic member in a concentric arrangement as the catheter is being produced, but also aids in maintaining the connection, which is preferably a bonded connection, between the adapting member and the ceramic member. The adapting member, in particular its distal protrusion, and/or the stiffening tube can hold the capillary (second) tube within the catheter by means of a bonded connection.

The ceramic member can also comprise a distal section exhibiting an outer diameter which gradually decreases and in particular tapers in a distal direction. As already mentioned above, the stiffening tube can provide a first barrier against any backflow of the therapeutic agent. However, in certain circumstances, the therapeutic agent may yet manage to pass this "stepped" barrier in a proximal direction. In this case, the decreasing-diameter section of the ceramic member provides a second barrier exhibiting a diameter which increases gradually in a proximal direction and thus hinders any backflow of the therapeutic agent. Even though the increase in the outer diameter is greater than that of the "stepped" barrier provided by the stiffening tube, providing an even more effective backflow barrier, the gradual increase in the diameter of the distal section of the ceramic member helps to avoid any damage to the surrounding tissue as the catheter is advanced through the brain. In general, the decreasing-diameter section of the ceramic member can exhibit a tapered, concave, convex or other, more complex shape, as long as the outer diameter of the catheter situated radially on the outside of the ceramic member decreases in a distal direction, in order to avoid injury to the surrounding tissue which would additionally compromise the infusion.

The outer diameter of a proximal section of the ceramic member can be constant in the longitudinal direction of the catheter. It is also conceivable for the outer diameter of the catheter to reach its greatest value at the position of the ceramic member and to not exceed this maximum diameter within the section which is proximal with respect to the ceramic member.

In accordance with another preferred embodiment of the present invention, the shrink-fit tube extends beyond the distal opening of the ceramic member and in particular up to the distal opening of the stiffening tube, wherein a curable agent is provided between the shrink-fit tube and the ceramic member, specifically at the distal end of the ceramic member and underneath the shrink-fit tube.

Providing such a curable agent between the shrink-fit tube and the ceramic member smoothens any sharp edges or sudden increases in the outer diameter of the catheter, which helps to prevent damage to the surrounding tissue when the catheter is advanced to the desired treatment region.

The shrink-fit tube can also be shrunk directly onto the outer surface of the ceramic member and/or directly onto the outer surface of the first tube and/or onto the outer surface of the stiffening tube.

As already indicated above, the ceramic member can be clearly located in ultrasound, MR and CT images, such that it is preferable to provide the distal opening of the stiffening tube which forms the first backflow barrier and/or the decreasing-diameter section of the ceramic member which forms the second backflow barrier at a predetermined position relative to the distal opening of the second tube. If the spatial position (i.e. spatial location and/or spatial orientation) of the opening of the second tube which dispenses the therapeutic agent is known, due to the known position of the ceramic member, then the position of the first and second backflow barriers can aid in predicting the distribution of the therapeutic agent within the patient's tissue at the target region.

For locating purposes, the catheter of the present invention can also comprise at least one additional ceramic member which can be detected in ultrasound, MR and CT images and which is disposed at a predetermined position relative to the catheter, in particular relative to the distal opening of the second tube. It is also conceivable for any part of the catheter made of radiolucent material or material which is invisible in ultrasound and MR images to comprise radiopacifiers or ultrasound-relevant contrast agents or MR-relevant contrast agents, respectively, so as to render the respective parts of the catheter visible and therefore detectable.

In order to allow an infusion over a longer period of time, the proximal section and in particular the first and second tubes are configured to allow the proximal section of the catheter to be "tunnelled". For this purpose, the catheter of the present invention, in particular its proximal section, can also comprise hollow head fixation means which define a volume for accommodating the first tube so as to attach the catheter directly to a bony anatomical structure, wherein the head fixation means in particular comprise a hollow bone fixation member which has an outer bone fixation thread or other expedient bone-engaging means at its distal end, a threaded proximal end or other expedient attaching means, and a receptacle for receiving a correspondingly formed portion of a tightening and loosening tool. The head fixation means can also comprise: a soft hollow tube, preferably made of silicone, which is accommodated in the bone fixation member; a hollow adapting member which is configured to allow the second tube, which leaves the fixation member, to be tunnelled without kinking, wherein the adapting member has a distal thread or other expedient attachment means which corresponds to the threaded proximal end of the bone fixation member; and a covering member which can be attached to the open proximal end of the adapting member in order to provide a cover/seal for the opening of the head fixation means.

More specifically, the soft hollow tube accommodated within the hollow bone fixation member is squeezed by screwing the hollow adapting member onto the hollow bone fixation member, whereupon the inner diameter of the soft hollow silicone tube decreases, such that the silicone tube firmly abuts the outer surface of the first catheter tube and the catheter is thus held firmly in place relative to the head fixation means. The inner diameter of the hollow adapting member can also gradually increase in a proximal direction, thus avoiding any sharp edges, such that the first and second catheter tubes which extend through the adapting member do not kink when they are bent substantially at a right angle along the inner surface of the adapting member, so as to allow the catheter to be tunnelled. The covering member of the head fixation means can also be attached to the adapting member by means of a bayonet coupling or any other expedient coupling, such that the opening in the patient's skull into which the catheter extends is covered and so protected against infection.

Another aspect of the present invention relates to an agent delivery system which comprises a catheter as described above and a stylet which comprises a handle portion and a hollow ceramic shaft which is configured to be accommodated within the annular cavity of said catheter, wherein a (thermal) shrink-fit tube is disposed radially on the outside of the ceramic shaft and in particular extends over at least the length of the ceramic shaft.

In other words, the scope of the present invention also includes a stylet for advancing the catheter of the present invention through tissue, in particular brain tissue, to a desired treatment region. As already described above, ceramic materials such as are also used for the stylet shaft are very stiff and therefore allow the catheter to be placed very precisely, but are also brittle and may break when used in an elongated and/or thin stylet shaft or when used inappropriately. The present invention therefore also provides a shrink-fit tube for the stylet shaft which can extend over the entire length of the ceramic part of the stylet shaft, in order to maintain the integrity of the stylet even after the stylet shaft suffers breakage.

In order to allow the spatial position of the catheter and/or the stylet to be determined, the catheter and/or stylet can comprise tracking means which are in particular provided at the handle portion of the stylet and/or the distal section of the catheter and which allow the catheter and/or stylet to be tracked, wherein the tracking means comprise one or more tracking markers which allow the spatial position of the catheter and/or stylet to be determined during the placement procedure by means other than CT images and which are selected from the group consisting of:

optical, in particular IR tracking markers;
EM tracking markers;
MRI-compatible tracking markers.

In the following, the invention is described with reference to the enclosed figures which represent a preferred embodiment of the invention without limiting the invention to the specific features shown in the figures.

Figure 1:
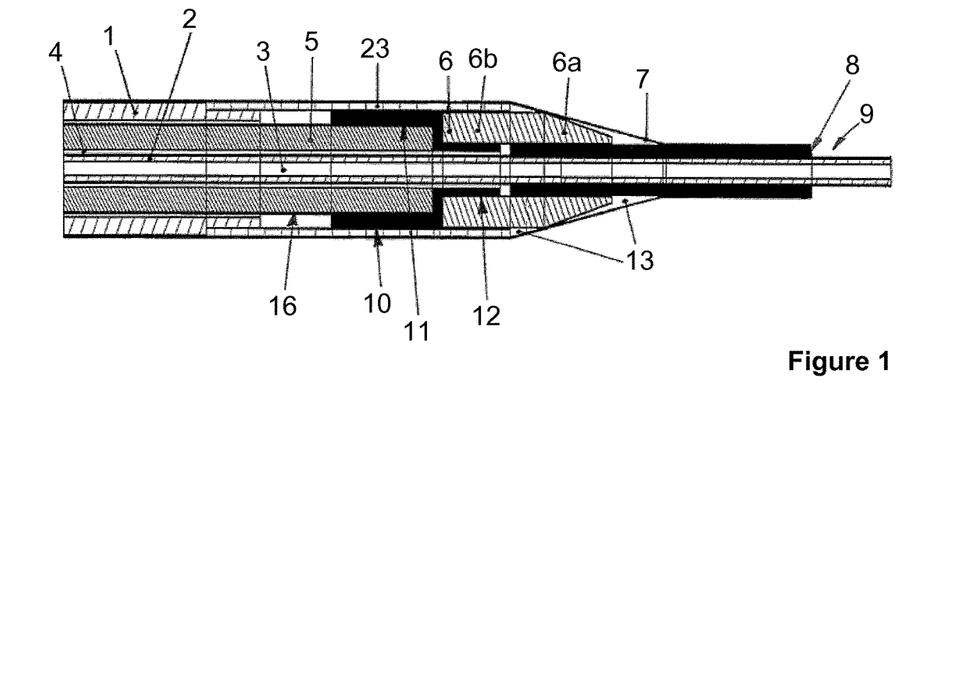
FIG. 1 shows the distal tip of an embodiment of the agent delivery catheter of the present invention.

As shown in FIG. 1, the catheter of the present invention comprises a first tube 1 and a second tube 2 which defines an agent delivery lumen 3 and which protrudes with it's distal end 9 from a distal opening of the first tube 1, wherein the first tube 1 is coupled to the second tube 2 via a stiffening tube 8, a ceramic member 6 and a third tube 23 which are adhesively connected to each other.

An adapting member 10 is also provided, at the distal end of the ceramic member 6, wherein the protruding section 12 of the adapting member 10 assists in aligning the adapting member 10 relative to the ceramic member 6 when the adapting member 10 is bonded to the ceramic member 6. The adapting member 10 also comprises a circumferential inner surface 11 which holds the outer surface 16 of stylet shaft 5 in place by means of a frictional fit, such that the stylet shaft 5 does not unintentionally leave the adapting member 10 and the cavity 4 formed between the first tube 1 and the second tube 2 when the stylet shaft 5 is pulled slightly in order to reposition the catheter tip.

As can also be seen in FIG. 1, the third tube 23 is bonded to the first tube 1 at a stepped distal portion of the first tube 1 and to the ceramic member 6 at a cylindrical portion 6b which exhibits a constant outer diameter.

Since the brittle material properties of the ceramic member 6 do not permit the distal portion 6a to taper until the wall thickness of the distal opening of the ceramic member 6 reaches zero, the tapered section 6a of the ceramic member 6 ends at a wall thickness which is still sufficient to avoid breakage at the distal end of the ceramic member 6.

The wall thickness of the stiffening tube 8 determines the strength of a backflow barrier which is provided at the distal end of the stiffening tube 8. In order to avoid damage to surrounding tissue, the increase in diameter in the region of the tapered section 6a of the ceramic member 6 is "smoothened" by filling the steps (incremental changes) in the outer diameter of the catheter with a curable agent 13 which is provided between the stiffening tube 8, the ceramic member 6 and the shrink-fit tube 7. The shrink-fit tube 7 is shrunk onto the outer surface of the catheter, starting from the distal end of the stiffening tube 8 and extending over at least the proximal end of the ceramic member 6.

Figure 2:
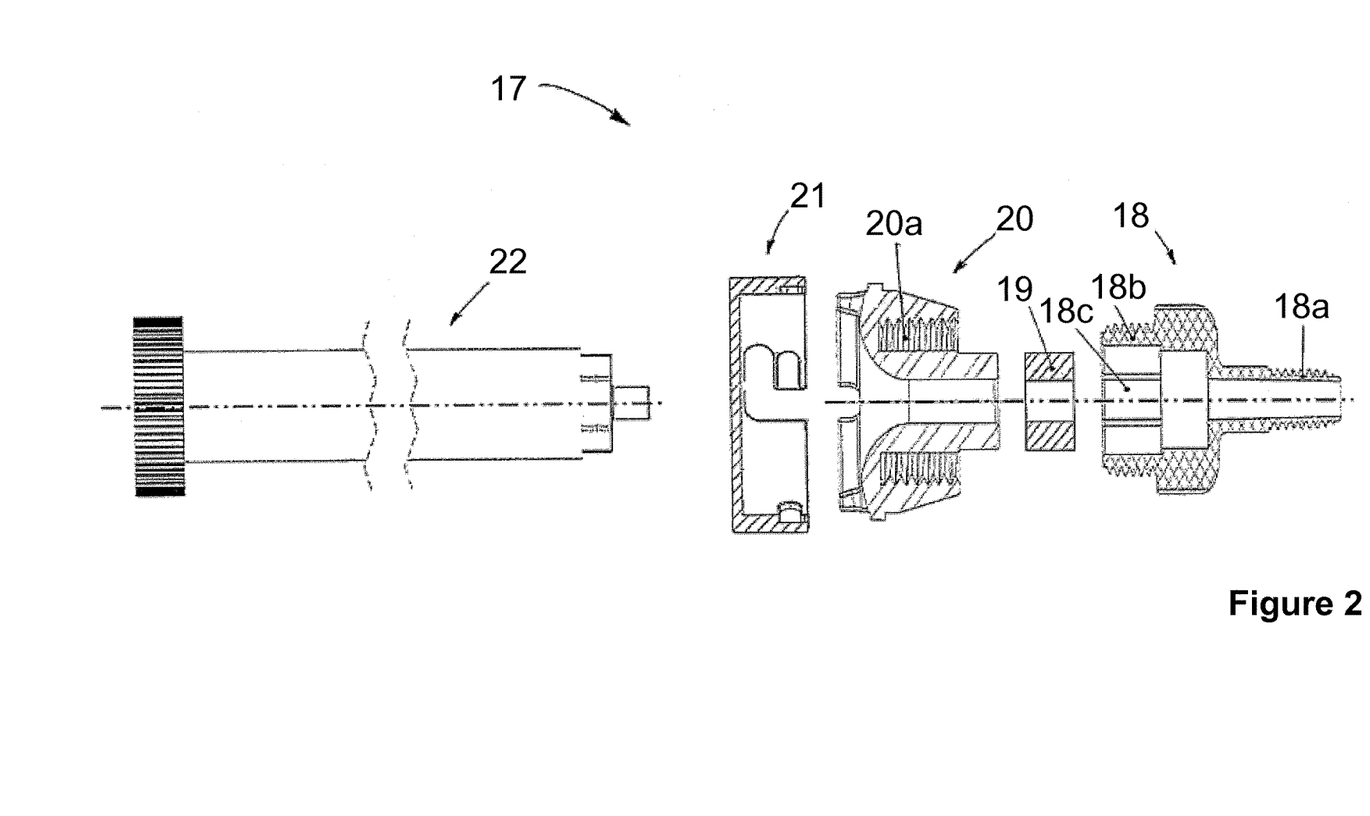
FIG. 2 shows a hollow head fixation means such as can be used to fix the catheter of the invention to a bony structure of the patient when a therapeutic agent is to be delivered over a longer period of time.

FIG. 2 shows a hollow head fixation means 17 comprising a hollow bone fixation member 18, the threaded portion 18a of which can be screwed into a corresponding bore in a patient's skull using a tightening and loosening tool 22 which fits into a corresponding portion of the hollow bone fixation member 18 having a lumen 18c. Another outer thread 18b allows a hollow adapting member 20, having a corresponding inner thread 20a, to be screwed onto the hollow bone fixation member 18, thereby squeezing the soft hollow silicone tube 19. The inner diameter of the tube 19 decreases as the tube 19 is squeezed, such that the tube 19 firmly abuts the outer surface of the first tube 1 and the catheter is thus held firmly in place for the duration of the infusion.

As can be seen from FIG. 2, the hollow bone fixation member 18, the soft hollow silicone tube 19 and the hollow adapting member 20 have a common central axis, wherein the adapting member 20 and a covering member 21 are configured to receive a catheter bent at the proximal end of the hollow adapting member 20 by an angle of substantially 90°, wherein the rounded inner edge of the hollow adapting member 20 prevents the catheter from kinking.

In order to seal the opening of the fixation means, a covering member 21 is attached to the distal end of the hollow adapting member 20.

Figure 3:
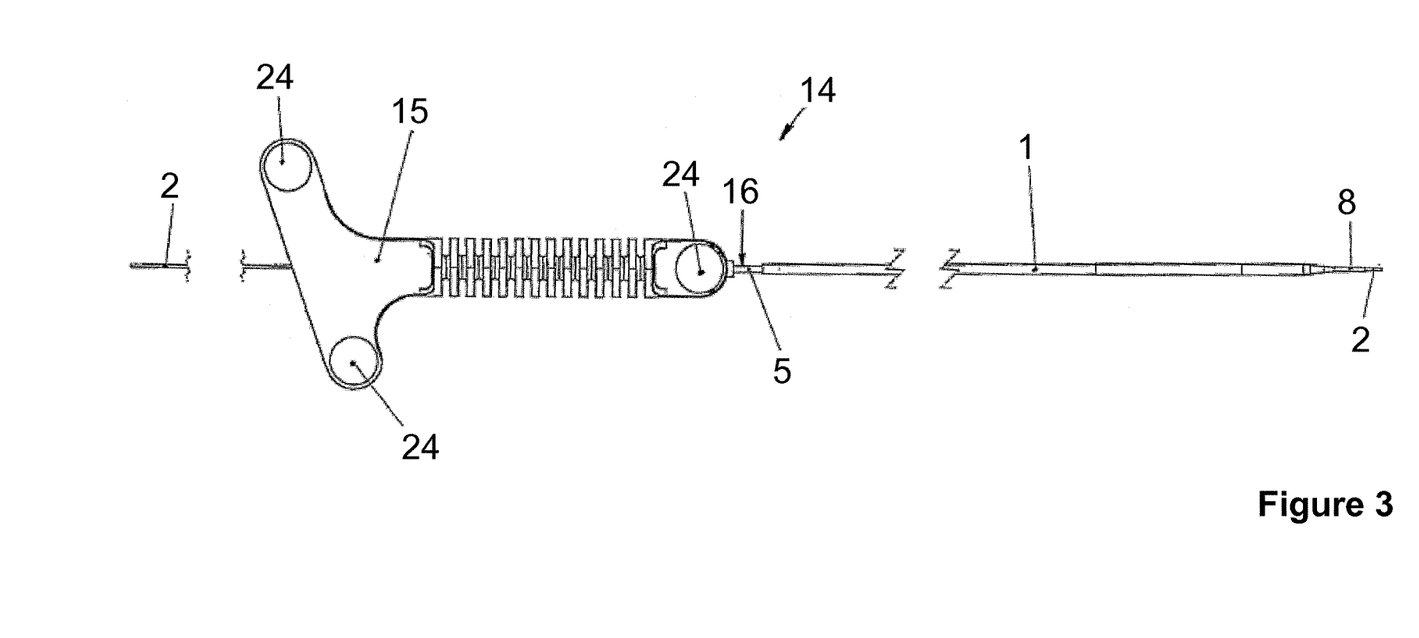
FIG. 3 shows an embodiment of an agent delivery system according to the present invention, comprising a stylet and a catheter.

FIG. 3 shows an agent delivery system according to the present invention, comprising: a stylet 14; and a catheter which comprises inter alia a first hollow tube 1, a second hollow tube 2 and a stiffening tube 8. The stylet 14 comprises a handle portion 15 which can be grasped by a surgeon in order to advance or retract the catheter through the patient's tissue and to withdraw the shaft 5 of the stylet 14 from the catheter in a proximal direction. The stylet shaft 5 is made of a ceramic material, preferably alumina, and specifically contains high-purity alumina (greater than 99%, for example 99.8%). It is covered with a protective shrink-fit tube [[16]]. The handle portion 15 further comprises tracking markers 24 which allow the spatial position of the stylet 14 and the catheter to be determined, relative to a target region to be treated, by means of an optical medical tracking system.

Figure 4:
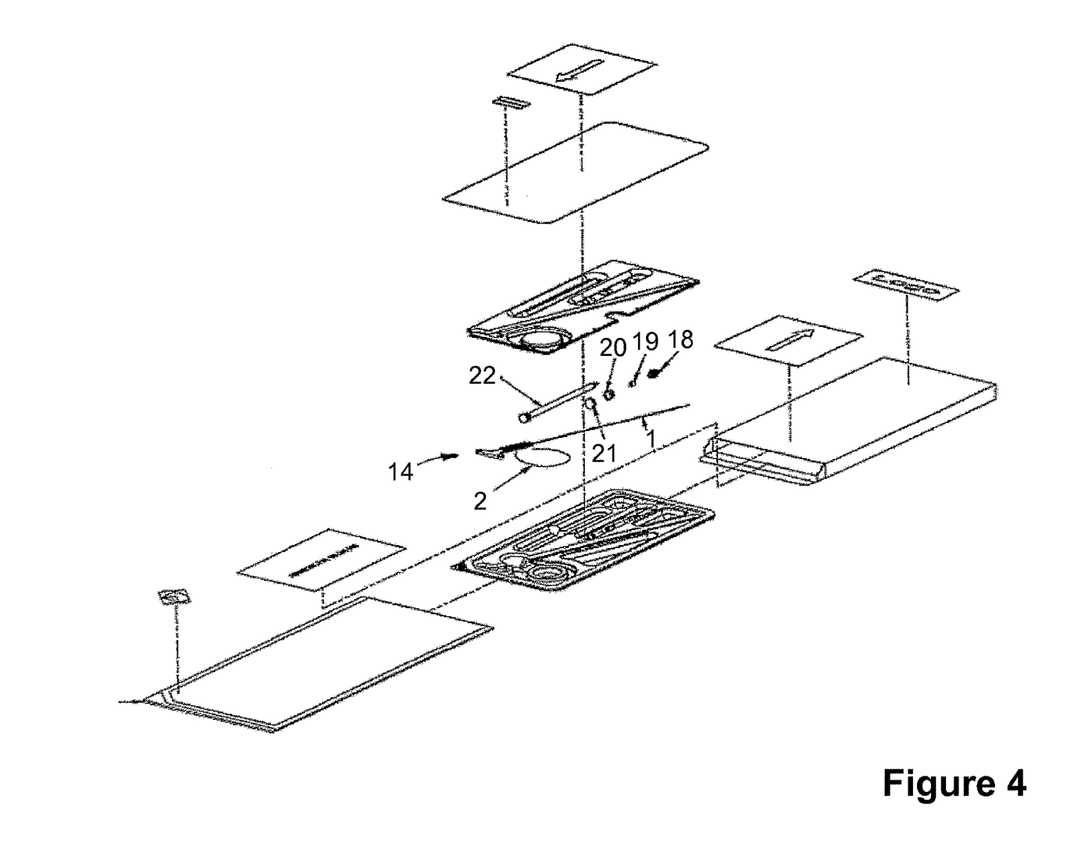
FIG. 4 shows a retail package comprising an embodiment of the agent delivery system according to the present invention.

FIG. 4 shows a retail package comprising an embodiment of the agent delivery system according to the present invention, such as has been described further above, wherein all of the sterilised components are sealed within a plastic tray which is in turn accommodated within cardboard packaging.

The invention claimed is:

1. An agent delivery catheter, comprising a first hollow tube and a second hollow tube which protrudes from a distal opening of the first hollow tube and defines an agent delivery lumen extending along the entire length of the catheter, wherein: a distal end of the first tube is coupled to the second tube to form an annular cavity between the first tube and the second tube, the annular cavity being configured to accommodate a retractable stylet shaft, wherein a ceramic member which is disposed at the distal end of the first tube encompasses the second tube and couples the first tube to the second tube, wherein a protective shrink-fit tube is disposed radially on the outside of the ceramic member and extends over at least a length of the ceramic member, and wherein the agent deliver catheter further comprises an adapting member which is disposed on and coupled to a proximal end of the ceramic member and configured to receive a distal end of the retractable stylet shaft.

2. The agent delivery catheter according to claim 1, wherein the second tube protrudes from a distal opening of the ceramic member, wherein a stiffening tube protrudes from the distal opening of the ceramic member and extends over at least a part of a protruding portion of the second tube.

3. The agent delivery catheter according to claim 2, wherein the stiffening tube is disposed radially between the second tube and the ceramic member.

4. The agent delivery catheter according to claim 1, wherein the adapting member comprises a circumferential inner surface which is configured to establish a frictional fit or positive fit between the distal end of the stylet shaft and the adapting member.

5. The agent delivery catheter according to claim 1, wherein the adapting member comprises a protrusion which extends centrally in a distal direction from a distal end of the adapting member into a proximal opening of the ceramic member.

6. The agent delivery catheter according to claim 1, wherein an outer diameter of a distal section of the ceramic member decreases in a distal direction, or an outer diameter of a proximal section of the ceramic member is constant.

7. The agent delivery catheter according to claim 1, wherein the shrink-fit tube extends beyond a distal opening of the ceramic member, and wherein a curable agent is provided between the shrink-fit tube and the ceramic member.

8. The agent delivery catheter according to claim 7, wherein the shrink-fit tube extends up to a distal opening of a stiffening tube.

9. The agent delivery catheter according to claim 1, wherein a diameter of the portion of the catheter situated proximally with respect to the ceramic member is substantially constant or is smaller than a diameter of the ceramic member.

10. The agent delivery catheter according to claim 1, wherein the shrink-fit tube is shrunk directly onto the outer surface of the ceramic member.

11. The agent delivery catheter according to claim 10, wherein the shrink-fit tube is shrunk directly onto an outer surface of the first tube or onto an outer surface of a stiffening tube.

12. The agent delivery catheter according to claim 1, wherein a distal opening of a stiffening tube or the ceramic member is disposed at a predetermined position relative to a distal opening of the second tube.

13. The agent delivery catheter according to claim 1, further comprising at least one additional ceramic member at a predetermined position relative to the catheter.

14. The agent delivery catheter according to claim 1, wherein the catheter is configured to allow tunnelling.

15. The agent delivery catheter according to claim 1, further comprising a hollow head fixation member which defines a volume for accommodating the first tube for attaching the catheter directly to a bony anatomical structure, wherein the head fixation member comprises a hollow bone fixation member which has an outer bone fixation thread at its distal end, a threaded proximal end, and a receptacle for receiving a correspondingly formed portion of a tightening and loosening tool, wherein the head fixation member also comprises: a soft hollow silicone tube which is accommodated in the bone fixation member; a hollow adapting member which is configured to allow the second tube, which leaves the fixation member, to be tunnelled without kinking, wherein the hollow adapting member has a distal thread which corresponds to the threaded proximal end of the bone fixation member; and a covering member which is adapted to be attached to an open proximal end of the hollow adapting member for providing a cover or a seal for an opening of the head fixation member.

16. An agent delivery system, comprising a catheter according to claim 1, and a stylet which comprises a handle portion and a ceramic shaft which is configured to be accommodated within the annular cavity of said catheter, wherein a shrink-fit tube is disposed radially on the outside of the ceramic shaft and extends over at least the length of the ceramic shaft.

17. The agent delivery system according to claim 16, further comprising tracking members at the handle portion of the stylet or the distal section of the catheter, which allow the catheter or stylet to be tracked, wherein the tracking members comprise one or more tracking markers selected from the group consisting of:
optical, IR tracking markers;
EM tracking markers;
MRI-compatible tracking markers.

18. The agent delivery catheter according to claim 1, wherein the adapting member is configured to be releasably secured to the distal end of the stylet shaft via a positive fit or a frictional fit.

19. The agent delivery catheter according to claim 1, wherein the ceramic member is disposed distally with respect to the distal opening of the first tube or couples the first tube to the second tube via a third hollow tube which encompasses the first tube and the ceramic member.

20. An agent delivery catheter, comprising a first hollow tube and a second hollow tube which protrudes from a distal opening of the first hollow tube and defines an agent delivery lumen extending along the entire length of the catheter, wherein: a distal end of the first tube is coupled to the second tube to form an annular cavity between the first tube and the second tube, the annular cavity being configured to accommodate a retractable stylet shaft, wherein a ceramic member which is disposed at the distal end of the first tube encompasses the second tube and couples the first tube to the second tube, and wherein a protective shrink-fit tube is disposed radially on the outside of the ceramic member and extends over at least a length of the ceramic member, further comprising a hollow head fixation member which defines a volume for accommodating the first tube for attaching the catheter directly to a bony anatomical structure, wherein the head fixation member comprises a hollow bone fixation member which has an outer bone fixation thread at its distal end, a threaded proximal end, and a receptacle for receiving a correspondingly formed portion of a tightening and loosening tool, wherein the head fixation member also comprises: a soft hollow silicone tube which is accommodated in the bone fixation member; a hollow adapting member which is configured to allow the second tube, which leaves the fixation member, to be tunnelled without kinking, wherein the adapting member has a distal thread which corresponds to the threaded proximal end of the bone fixation member; and a covering member which is adapted to be attached to an open proximal end of the adapting member for providing a cover or a seal for an opening of the head fixation member.

* * * * *